United States Patent [19]

Grollier et al.

[11] Patent Number: 5,259,849
[45] Date of Patent: * Nov. 9, 1993

[54] COMPOSITION BASED ON QUINONE DYESTUFFS FOR USE IN HAIR DYEING AND PROCESS FOR THE PRESERVATION OF QUINONE DYESTUFFS

[75] Inventors: Jean F. Grollier, Paris; Jean Cotteret, Franconville, both of France

[73] Assignee: L'Oreal, Paris, France

[ * ] Notice: The portion of the term of this patent subsequent to Jan. 23, 2007 has been disclaimed.

[21] Appl. No.: 896,573

[22] Filed: Jun. 10, 1992

Related U.S. Application Data

[63] Continuation of Ser. No. 383,001, Jul. 21, 1989, abandoned, which is a continuation of Ser. No. 490,111, Apr. 29, 1983, abandoned.

[30] Foreign Application Priority Data

Apr. 29, 1982 [LU] Luxembourg ............................ 84122

[51] Int. Cl.$^5$ .......................... A61K 7/13; C09B 67/00
[52] U.S. Cl. ........................................... 8/405; 8/428; 8/435; 8/609; 8/610; 8/611; 8/662; 8/663
[58] Field of Search .................. 8/405, 428, 435, 609, 8/610, 611, 907, 662, 663

[56] References Cited

U.S. PATENT DOCUMENTS

| | | | |
|---|---|---|---|
| 2,695,259 | 11/1954 | Charle | 8/433 |
| 3,041,244 | 6/1962 | Feit et al. | 8/408 |
| 4,184,844 | 1/1980 | Grollier et al. | 8/407 |
| 4,208,183 | 6/1980 | Grollier et al. | 8/609 |
| 4,602,913 | 7/1986 | Grollier et al. | 8/405 |
| 4,832,943 | 5/1989 | Grollier et al. | 424/63 |
| 4,867,751 | 9/1989 | Lang et al | 8/428 |
| 4,888,026 | 12/1989 | Lang et al. | 8/405 |
| 4,895,575 | 1/1990 | Hocquaux et al. | 8/424 |
| 4,971,596 | 11/1990 | Grollier | 8/424 |

FOREIGN PATENT DOCUMENTS

| | | |
|---|---|---|
| 0517244 | 12/1954 | Belgium . |
| 616362 | 7/1935 | Fed. Rep. of Germany . |
| 2473310 | 7/1981 | France . |
| 1252368 | 11/1971 | United Kingdom . |
| 1273055 | 5/1972 | United Kingdom . |

*Primary Examiner*—Linda Skaling
*Assistant Examiner*—William S. Parks
*Attorney, Agent, or Firm*—Cushman, Darby & Cushman

[57] ABSTRACT

The invention relates to compositions, which are stable on storage, of certain benzoquinone and naphthoquinone dyestuffs in an anhydrous solvent containing a non-ionic surface-active agent.

8 Claims, No Drawings

COMPOSITION BASED ON QUINONE DYESTUFFS FOR USE IN HAIR DYEING AND PROCESS FOR THE PRESERVATION OF QUINONE DYESTUFFS

This is a continuation of application No. 07/383,001, filed Jul. 21, 1989, now abandoned, which is a continuation of application No. 06/490,111 filed Apr. 29, 1983, now abandoned.

The present invention relates to a process making it possible to preserve quinone dyestuffs which are certain benzoquinones or naphthoquinones, to the compositions making it possible to preserve these dyestuffs, and to the use of these compositions in the preparation of hair-dyeing compositions.

2-Hydroxynaphthoquinones and benzoquinones are dyestuffs which are in themselves known but most of them have not been used hitherto in hair dyeing. The use of such dyestuffs in hair dyeing has formed the subject of Luxembourg Patent Applications Nos 83 807 and 83 806 corresponding to Ser. No. 445,967 and 445,705 filed on Dec. 1, 1982.

2-Hydroxy-1,4-naphthoquinone, also called lawsone, which is one of the dyestuffs responsible for henna dyeing, has also been known for a long time.

The 2-hydroxynaphthoquinones mentioned in Luxembourg Patent Application No 83 806(Ser. No. 445,705), correspond to the following formula:

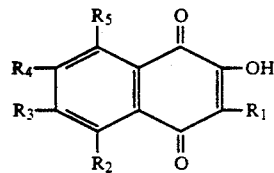

in which $R_1$ denotes hydrogen, hydroxyl, alkoxy, nitro, halogen, alkyl or acyl and $R_2$, $R_3$, $R_4$ and $R_5$ independently of one another denote hydrogen, hydroxyl, alkoxy, alkyl or acyl, at least one of the substituents $R_1$ to $R_5$ being other than hydrogen. In this formula, $R_2$ and $R_5$ cannot simultaneously denote hydroxyl if $R_1$, $R_3$ and $R_4$ denote hydrogen. The alkoxy or alkyl groups preferably denote groups having 1 to 4 carbon atoms, and the acyl groups have from 2 to 4 carbon atoms.

The benzoquinones disclosed in Luxembourg Patent Application No 83 807 (Ser. No. 445,967) correspond to the formula:

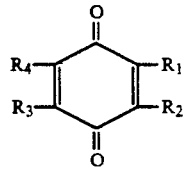

in which $R_1$ and $R_3$ independently of one another denote hydrogen, hydroxyl, alkoxy or optionally hydroxylated alkyl and $R_2$ and $R_4$ independently of one another denote hydrogen, hydroxyl, alkoxy, alkyl having 1 to 3 carbon atoms or phenyl optionally substituted by OH, these compounds having at most two alkyl or alkoxy groups on the quinone nucleus.

These compounds have good tinctorial strength on hair when they are used as direct dyestuffs. However, they present certain problems insofar as they are sparingly soluble, in particular in water, and insofar as they are also unstable in aqueous solution during storage.

One way of overcoming this problem is to use them in powder form with other pulverulent products serving as carriers. On dilution, a coloring poultice can be obtained.

This method of use, although very advantageous, nevertheless has the shortcoming that the dyestuff must be dissolved at the time of use, that is to say at the time when the powder is made into a paste with water. The tinctorial strength is therefore limited by the rate of solubilization and the solubilization limit of the above-mentioned dyestuffs.

We have discovered that, although these dyestuffs lose their tinctorial strength, on storage, in aqueous compositions normally used in hair dyeing, certain benzoquinones or naphthoquinones preserve this tinctorial strength in a surprising way during storage in anhydrous solvents.

The present invention accordingly provides solutions of certain quinone dyestuffs in an anhydrous solvent or mixture of anhydrous solvents as well as a process for the preservation of these dyestuffs in the anhydrous solvent or solvents.

The solutions or compositions according to the invention are essentially characterised in that they contain at least one quinone dyestuff carrying at least one OH or methoxy groups and at most two methoxy or four OH groups corresponding to the formulae:

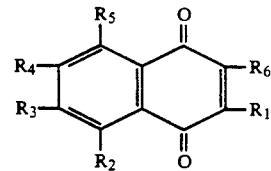 (I')

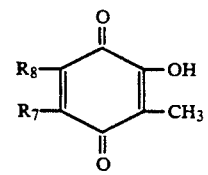 (II')

in which $R_1$, $R_2$, $R_3$, $R_4$, $R_5$, $R_6$, $R_7$ and $R_8$ have the meanings below:

| Compound | $R_1$ | $R_2$ | $R_3$ | $R_4$ | $R_5$ | $R_6$ | $R_7$ | $R_8$ |
|---|---|---|---|---|---|---|---|---|
| 1 | H | H | H | H | H | OH | — | — |
| 2 | OH | H | H | H | H | OH | — | — |
| 3 | H | H | H | OH | H | OH | — | — |
| 4 | H | H | H | H | $OCH_3$ | OH | — | — |
| 5 | $OCH_3$ | H | H | H | H | OH | — | — |
| 6 | H | OH | H | H | H | OH | — | — |
| 7 | H | H | $OCH_3$ | H | H | OH | — | — |

-continued

| Compound | $R_1$ | $R_2$ | $R_3$ | $R_4$ | $R_5$ | $R_6$ | $R_7$ | $R_8$ |
| --- | --- | --- | --- | --- | --- | --- | --- | --- |
| 8 | H | OH | H | H | H | $OCH_3$ | — | — |
| 9 | $CH_3$ | H | H | H | H | OH | — | — |
| 10 | H | $OCH_3$ | H | H | $OCH_3$ | OH | — | — |
| 11 | $OCH_3$ | OH | H | H | H | H | — | — |
| 12 | H | H | OH | H | H | OH | — | — |
| 13 | H | H | H | H | OH | OH | — | — |
| 14 | $CH_3$ | H | H | H | OH | OH | — | — |
| 15 | H | H | OH | OH | H | OH | — | — |
| 16 | OH | OH | H | H | OH | OH | — | — |
| 17 | — | — | — | — | — | — | OH | $OCH_3$ |
| 18 | — | — | — | — | — | — | $OCH_3$ | $OCH_3$ |
| 19 | — | — | — | — | — | — | OH | H | in an anhydrous solvent or mixture of anhydrous solvents, in the presence of a non-ionic surface-active agent.

The term "anhydrous" is to be understood as meaning solvents or mixtures of solvents which do not contain more than 1% of water. These solvents are cosmetically acceptable and include, in particular, lower (e.g. of 1 to 6 carbon atoms) saturated monoalcohols such as ethanol and isopropanol, long-chain (e.g. of at least 7 carbon atoms) saturated monoalcohols such as cetyl alcohol, polyols such as alkylene glycols, for example ethylene glycol, propylene glycol, glycerol and diethylene glycol, glycol ethers such as mono-, di- and tri-ethylene glycol monoalkyl ethers, for example ethylene glycol monoethyl ether, ethylene glycol monobutyl ether and diethylene glycol monoethyl ether, esters such as ethylene glycol monomethyl ether acetate and ethylene glycol monoethyl ether acetate, and saturated fatty acid esters of saturated lower alcohols, such as isopropyl myristate or palmitate. The preferred compositions contain, in particular, ethanol, cetyl alcohol, propylene glycol, ethylene glycol monoethyl ether or ethylene glycol monobutyl ether.

In a preferred embodiment of the invention the anhydrous medium consists of one or more of the abovementioned anhydrous solvents and of one or more anhydrous non-ionic surface-active agents so that the composition contains at least 15% of solvent(s) and at least 20% of surface-active agent(s).

The non-ionic surface-active agents which can be used are chosen, in particular, from amongst polyoxyethyleneated fatty alcohols, polyoxyethyleneated alkylphenols or naphthols and polyglycerolated fatty alcohols.

The dyestuffs used according to the invention are suitably present in these compositions, by themselves or in association, in amounts from 0.001 to 5% by weight and preferably from 0.005 to 2% by weight, relative to the total weight of the anhydrous composition.

The compositions according to the invention can contain an anhydrous alkaline or acidifying agent. Examples of agents used for this purpose are citric acid, ascorbic acid, acetic acid, lactic acid and alkanolamines, preferably those which are completely substituted on the amine group, for example dimethylaminoethanol.

When an acidifying agent is used, the particularly preferred dyestuffs are dyestuffs 1 to 6 and 8 to 19 in the above table, and in the case where an alkalizing agent is used, the particularly preferred dyestuffs are dyestuffs 2 to 7 in the above table.

Preferred embodiments of the invention therefore consist of these two types of composition, namely, on the one hand, compositions having an acid pH after dilution with water and containing dyestuffs 1 to 6 and 9 to 11, and, on the other hand, compositions having an alkaline pH after dilution with water and containing dyestuffs 2 to 8.

Apart from the compounds described above, the anhydrous compositions according to the invention can contain numerous additives, the only condition being that they contain less than 1% of water.

For this purpose, there may be mentioned, amongst the other additives, perfumes, sequestering agents, thickeners, hair-treating agents, antioxidants, vegetable or mineral oils, preservatives and organic salts.

The compositions can also contain other dyestuffs intended for use in hair dyeing and which are direct dyestuffs. It is possible, in particular, to make use of natural direct dyestuffs of low stability in aqueous solution. The following may be mentioned in particular amongst these types of dyestuffs: haematoxylin, which is the dyestuff present in logwood, brasilin, which is the dyestuff present in brazilwood, and also henna extract. Examples which may be mentioned of other coloring extracts obtained from coloring plants are extracts of madder, wild camomile, curcuma and annatto.

The direct dyestuffs, other than those corresponding to the formulae (I') and (II'), which can be used according to the invention are in themselves well known; they include, in particular, anthraquinone dyestuffs, azo dyestuffs, triarylmethane dyestuffs, azine dyestuffs and nitrobenzene derivatives such as nitrophenylenediamines, nitroaminophenols, dinitroaminophenols, nitroaminobenzenes and nitrodiphenylamines. It is preferred to use anthraquinone dyestuffs and in particular the hydroxyanthraquinones described in French Patent Application No. 82/03,294 corresponding to U.S. Ser. No. 353,003 filed on Feb. 26, 1982, the disclosure of which is hereby incorporated by reference.

The dyestuffs other than those of the formula (I') or (II') are suitably present in the anhydrous dyeing compositions according to the invention in amounts from 0.01 to 3% by weight, preferably from 0.05 to 2% by weight, relative to the total weight of the anhydrous composition.

The compositions according to the invention can be stored for long periods without there being any deterioration in the tinctorial strength of the dyestuffs corresponding to the formulae (I') and (II').

These compositions can be applied as such to the wet hair or can be diluted just before use. In the latter case, at the time of dyeing, the compositions according to the invention are diluted with an aqueous solution so that the ratio of the composition according to the invention to the aqueous solution is generally 0.25:1 to 2:1 by weight. The aqueous solution can be pure water, but can also be in the form of an aqueous liquid of a greater or lesser degree of thickness, such as a carrier normally used in hair-dyeing compositions. In this case, the components of the cosmetic medium can be anhydrous or non-anhydrous, cosmetically acceptable ingredients normally used in this type of composition.

The mixture produced in this way is applied to the hair for, say, 1 minute to 1 hour, preferably from 5 minutes to 30 minutes. The hair is then rinsed, optionally shampooed and dried.

The Examples which follow further illustrate the present invention.

EXAMPLE 1

| | |
|---|---|
| 2-Hydroxy-3-methyl-5,6-dimethoxy-1,4-benzoquinone | 0.5 g |
| 2,3-Dihydroxy-1,4-naphthoquinone | 0.4 g |
| 2-Hydroxy-3-methoxy-1,4-naphthoquinone | 0.3 g |
| Anhydrous citric acid | 1 g |
| Anhydrous ethyl alcohol | 28.5 g |
| SINNOPAL NP 9 | 26.5 g |
| SINNOPAL NP 4 q.s.p. | 100 g |

This liquid is mixed with 1.5 times its weight of cold water at the time of use. The gel obtained is applied to light chestnut hair for 30 minutes. The hair is rinsed and dried and then possesses a purple-violet mahogany sheen.

The preservation of the tinctorial strength of the initial composition during storage is much better than that obtained on storing the final gel.

EXAMPLE 2

| | |
|---|---|
| 2-Hydroxy-1,4-naphthoquinone | 0.6 g |
| 2-Hydroxy-8-methoxy-1,4-naphthoquinone | 0.25 g |
| Anhydrous citric acid | 1 g |
| Anhydrous ethyl alcohol | 28.5 g |
| SINNOPAL NP 9 | 26.5 g |
| SINNOPAL NP 4 q.s.p. | 100 g |

This composition can be applied directly to wet hair; it can also be mixed with 1.5 times its weight of cold water at the time of use. The gel obtained is applied to light chestnut hair for 30 minutes. After the hair has been rinsed, it is dried. It then possesses an intense golden sheen.

In the liquid composition, the dyestuffs keep much better on storage than in the final gel applied to the hair.

EXAMPLE 3

| | |
|---|---|
| 2,3-Dihydroxy-1,4-naphthoquinone | 0.5 g |
| 2,5-Dihydroxy-1,4-naphthoquinone | 0.3 g |
| 8-Methoxy-2-hydroxy-1,4-naphthoquinone | 0.15 g |
| Anhydrous citric acid | 1 g |
| Cetyl alcohol | 24 g |
| MERGITAL CS 15 E | 23 g |
| EUTANOL G q.s.p. | 100 g |

This cream is mixed with an equal weight of warm water at the time of use. The creamy mixture obtained is applied to light chestnut hair. After an interval of 30 minutes, the hair is rinsed and dried. It then possesses a beige coppery sheen.

The three dyestuffs in the starting composition keep better in the latter than in the composition applied to the hair.

EXAMPLE 4

| | |
|---|---|
| 2-Hydroxy-3-methoxy-1,4-naphthoquinone | 0.7 g |
| 2,5,8-Trihydroxy-1,4-naphthoquinone | 0.05 g |
| N,N-Dimethylaminoethanol | 0.7 g |
| Anhydrous ethyl alcohol | 21.5 g |
| SINNOPAL NP 9 | 31 g |
| SINNOPAL NP 4 q.s.p. | 100 g |

This liquid is diluted with 1.5 times its weight of cold water to give a gel, which is applied to deep blond hair for 10 minutes. The hair is rinsed and dried. It then possesses an auburn sheen.

The dyestuffs keep much better in the liquid composition than in the final gel.

EXAMPLE 5

| | |
|---|---|
| 2,5-Dihydroxy-3-methyl-6-methoxy-1,4-benzoquinone | 0.7 g |
| 2,7-Dihydroxy-1,4-naphthoquinone | 0.3 g |
| Anhydrous citric acid | 1 g |
| Anhydrous ethyl alcohol | 28.5 g |
| SINNOPAL NP 9 | 26.5 g |
| SINNOPAL NP 4 q.s.p. | 100 g |

The above liquid is treated with 1.5 times its weight of water at the time of use. The gel obtained is applied to light chestnut hair for 30 minutes. The hair is then rinsed and dried. A purple-violet coloration is obtained.

The dyestuffs keep much better in the liquid composition than in the final gel applied to the hair.

EXAMPLE 6

| | |
|---|---|
| 2,3-Dihydroxy-1,4-naphthoquinone | 0.8 g |
| 2-N-(β-Hydroxyethyl)-amino-5-hydroxy-nitrobenzene | 0.15 g |
| Haematoxylin | 0.15 g |
| N,N-Dimethylaminoethanol | 1 g |
| Anhydrous ethyl alcohol | 24 g |
| SINNOPAL NP 9 | 28.5 g |
| SINNOPAL NP 4 q.s.p. | 100 g |

This liquid composition is mixed with 1.5 times its weight of water at the time of use. The gel obtained is applied to deep chestnut hair for 30 minutes, after which the hair is rinsed and dried. It then possesses a pearlescent ashen sheen.

The tinctorial strength is preserved much better during storage of the liquid composition than if the final gel is stored.

EXAMPLE 7

| | |
|---|---|
| 2,5-Dihydroxy-3-methyl-6-methoxy-1,4-benzoquinone | 1.1 g |
| 2-Hydroxy-3-methoxy-1,4-naphthoquinone | 0.35 g |
| 3-Carboxy-1,2,4-trihydroxy-9,10-anthraquinone | 0.1 g |
| Anhydrous citric acid | 1 g |
| Cetyl alcohol | 24 g |
| MERGITAL CS 15 E | 23 g |
| EUTANOL G q.s.p. | 100 g |

This composition, which forms a cream, is diluted with its own weight of warm water at the time of use. The cream obtained is applied to deep chestnut hair for 30 minutes. After rinsing and drying, the hair possesses a purple-violet sheen.

The preservation of the dyestuffs on storage is much better in the initial anhydrous composition than in the final composition applied to the hair.

EXAMPLE 8

| | |
|---|---|
| 2-Hydroxy-1,4-naphthoquinone | 0.20 g |
| 2,5-Dihydroxy-1,4-naphthoquinone | 0.15 g |
| Sodium 2-hydroxy-9,10-anthraquinone-3-sulphonate monohydrate | 0.40 g |
| Anhydrous citric acid | 1 g |
| Anhydrous ethyl alcohol | 28.5 g |
| SINNOPAL NP 9 | 26.5 g |
| SINNOPAL NP 4 q.s.p. | 100 g |

This composition is in the form of a liquid, which can be applied directly to wet hair or which is mixed with 1.5 times its weight of cold water at the time of use. The gel obtained is applied to light chestnut hair. After an interval of 40 minutes, the hair is rinsed and dried. It is dyed with a coppery beige sheen.

The storage stability of the dyestuffs is much better in the liquid composition than in the final gel.

EXAMPLE 9

| | |
|---|---|
| 2-Hydroxy-3-methoxy-1,4-naphthoquinone | 0.7 g |
| 2-Hydroxy-1,4-naphthoquinone | 0.25 g |
| Anhydrous citric acid | 1 g |
| Cetyl alcohol | 24 g |
| MERGITAL CS 15 E | 23 g |
| EUTANOL G q.s.p. | 100 g |

This cream is diluted with an equal weight of warm water at the time of use. The mixture obtained is a cream, which is applied to chestnut hair for 30 minutes. After rinsing and drying, the hair possesses an intense red coppery sheen.

The dyestuffs have a much better stability in the starting composition than in the composition applied to the hair.

EXAMPLE 10

| | |
|---|---|
| 2,3-Dihydroxy-1,4-naphthoquinone | 0.45 g |
| 2,5-Dihydroxy-1,4-naphthoquinone | 0.35 g |
| 2,7-Dihydroxy-1,4-naphthoquinone | 0.1 g |
| N,N-Dimethylaminoethanol | 1 g |
| Anhydrous ethyl alcohol | 24 g |
| SINNOPAL NP 9 | 28.5 g |
| SINNOPAL NP 4 q.s.p. | 100 g |

This liquid is diluted with 1.5 times its weight of water at the time of use. The gel obtained is applied to chestnut hair for 30 minutes. The hair is rinsed and then dried. It then possesses an ashen sheen.

The dyestuffs are more stable on storage in the anhydrous liquid carrier than they would be in the gel which is applied to the hair.

EXAMPLE 11

The following composition is prepared:

| | |
|---|---|
| 2,5-Dihydroxy-3-methyl benzoquinone | 0.3 g |
| 2,5-dihydroxy-1,4-naphthoquinone | 0.2 g |
| Anhydrous citric acid | 1 g |
| Anhydrous ethyl alcohol | 28.5 g |
| SINNOPAL NP 9 | 26.5 g |
| SINNOPAL NP 4 q s p | 100 g |

This composition is in the form of a liquid which can be applied directly to wet hair or it can be mixed at the time of use with 1.5× its weight of cold water. The gel obtained is applied to deep blond hair. After leaving it for 20 minutes, the hair is rinsed and dried. The hair is dyed with a mahogany sheen.

EXAMPLE 12

The following composition is prepared:

| | |
|---|---|
| 2-methoxy-5-hydroxy-1,4-naphthoquinone | 0.2 g |
| 2-hydroxy-8-methoxy-1,4-naphthoquinone | 0.3 g |
| 3-methoxy-5-hydroxy-1,4-naphthoquinone | 0.05 g |
| Anhydrous citric acid | 0.8 g |
| Anhydrous ethyl alcohol | 25 g |
| SINNOPAL NP 9 qsp | 100 g |

This liquid composition is applied directly to moistened blond hair.

After leaving it for 25 minutes, the hair is rinsed. It possesses a light golden sheen.

If the diluted composition is stored the three quinone dyestuffs are degraded whereas they are not degraded in the anhydrous composition kept under the same conditions.

EXAMPLE 13

The following composition is prepared:

| | |
|---|---|
| 2-hydroxy-3-methyl-1,4-naphthoquinone | 0.6 g |
| 2,5-dihydroxy-3-methyl-6-methoxy-1,4-benzoquinone | 0.07 g |
| Anhydrous citric acid | 1.2 g |
| Anhydrous ethyl alcohol | 30 g |
| Hydroxypropyl cellulose sold under the name KLUCEL G by HERCULES | 0.8 g |
| SINNOPAL NP 9 qsp | 100 g |

This thickened liquid is applied for 30 minutes to previously moistened blond hair.

After rinsing and drying, the hair possesses an ashen beige shade.

The conservation of the dyestuff in the anhydrous composition is better than that of a similar aqueous composition.

EXAMPLE 14

The following composition is prepared:

| | |
|---|---|
| 2,8-Dihydroxy-1,4-naphthoquinone | 0.5 g |
| 3-Methyl-2,8-dihydroxy-1,4-naphthoquinone | 0.2 g |
| 2,6,7-trihydroxy-1,4-naphthoquinone | 0.2 g |
| Anhydrous citric acid | 1 g |
| Cetyl alcohol | 24 g |
| Mergital CS 15 E | 23 g |
| Eutanol C q s p | 100 g |

This cream is diluted at the moment of use with an equal weight of warm water. A cream is obtained which is applied for 20 minutes to a pale chestnut head of hair which is then rinsed and dried. The hair now possesses a coppery sheen.

The dyestuffs are kept better in the anhydrous cream than in the aqueous composition applied to the head.

EXAMPLE 15

The following composition is prepared:

| | |
|---|---|
| 2-Hydroxy-5,8-dimethoxy-1,4-naphthoquinone | 0.05 g |
| 2,6-dihydroxy-1,4-naphthoquinone | 0.4 g |
| 2,3,5,8-tetrahydroxy-1,4-naphthoquinone | 0.3 g |
| 2-hydroxy-3-methyl-5,6-dimethoxy-1,4-benzoquinone | 0.1 g |
| Anhydrous citric acid | 1 g |
| Purified ethylene glycol monoethyl ether | 25 g |
| SINNOPAL NP 9 qsp | 100 g |

This liquid is applied for 25 minutes to a wetted pale chestnut head of hair. After rinsing and drying the hair possesses a coppery beige sheen.

The dyestuffs of this composition are more stable on storage than a corresponding aqueous composition.

In the foregoing examples, the tradenames used correspond to the following products:

| | |
|---|---|
| SINNOPAL NP 9 | Nonylphenol oxyethyleneated with 9 mols of ethylene oxide, sold by HENKEL |
| SINNOPAL NP 4 | Nonylphenol oxyethyleneated with 4 mols of ethylene oxide, sold by HENKEL |
| MERGITAL CS 15 E | Cetyl-stearyl alcohol containing 15 mols of ethylene oxide, sold by HENKEL |
| EUTANOL G | Octyldodecanol sold by HENKEL |

I claim:

1. An anhydrous storage-stable liquid or cream composition consisting essentially of
   (a) an anhydrous solvent present in an amount of at least 15 weight percent, said solvent being selected from the group consisting of a saturated alcohol, polyol, glycol ether, ester of an ethylene glycol monoalkyl ether and saturated fatty acid ester of a saturated lower alcohol,
   (b) a quinone dyestuff selected from the group consisting of
   (i) a quinone dyestuff of the formula

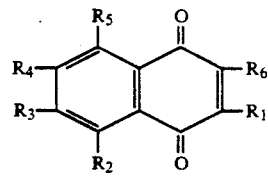

wherein $R_1$, $R_2$, $R_3$, $R_4$, $R_5$ and $R_6$ have the following indicated values:

| $R_1$ | $R_2$ | $R_3$ | $R_4$ | $R_5$ | $R_6$ |
|---|---|---|---|---|---|
| H | H | H | H | H | OH |
| OH | H | H | H | H | OH |
| H | H | H | OH | H | OH |
| H | H | H | H | OCH$_3$ | OH |
| OCH$_3$ | H | H | H | H | OH |
| H | OH | H | H | H | OH |
| H | H | OCH$_3$ | H | H | OH |
| H | OH | H | H | H | OCH$_3$ |
| CH$_3$ | H | H | H | H | OH |
| H | OCH$_3$ | H | H | OCH$_3$ | OH |
| OCH$_3$ | OH | H | H | H | H |
| H | H | OH | H | H | OH |
| H | H | H | H | OH | OH |
| CH$_3$ | H | H | H | OH | OH |
| H | H | OH | OH | H | OH |
| OH | OH | H | H | OH | OH | and
(ii) a quinone dyestuff of the formula

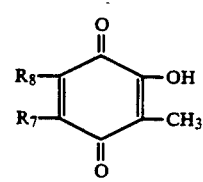

wherein $R_7$ and $R_8$ have the following indicated values

| $R_7$ | $R_8$ |
|---|---|
| OH | OCH$_3$ |
| OCH$_3$ | OCH$_3$ |
| OH | H | said dyestuff being present in an amount ranging from 0.001 to 5 percent by weight based on the total weight of said composition, and
(c) an anhydrous non-ionic surface-active agent present in an amount of at least 20 weight percent, said surface-active agent being selected from the group consisting of polyoxyethylenated fatty alcohol, polyoxyethylenated alkyl phenol, polyoxyethylenated naphthol and polyglycerolated fatty alcohol,
said composition not containing more than 1 percent by weight of water.

2. An anhydrous storage-stable liquid or cream composition consisting essentially of
   (a) an anhydrous solvent present in an amount of at least 15 weight percent, said solvent being selected from the group consisting of ethanol, isopropanol, cetyl alcohol, ethylene glycol, propylene glycol, glycerol, diethylene glycol, ethylene glycol monoethyl ether, ethylene glycol monobutyl ether, diethylene glycol monoethyl ether, ethylene glycol monomethyl ether acetate, ethylene glycol monoethyl ether acetate, isopropyl myristate and isopropyl palmitate,
   (b) a quinone dyestuff selected from the group consisting of
   (i) a quinone dyestuff of the formula

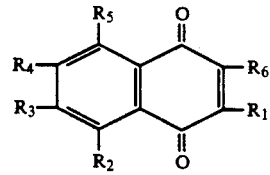

wherein $R_1$, $R_2$, $R_3$, $R_4$, $R_5$ and $R_6$ have the following indicated values:

| $R_1$ | $R_2$ | $R_3$ | $R_4$ | $R_5$ | $R_6$ |
|---|---|---|---|---|---|
| H | H | H | H | H | OH |

-continued

| R1 | R2 | R3 | R4 | R5 | R6 |
|---|---|---|---|---|---|
| OH | H | H | H | H | OH |
| H | H | H | OH | H | OH |
| H | H | H | H | OCH3 | OH |
| OCH3 | H | H | H | H | OH |
| H | OH | H | H | H | OH |
| H | H | OCH3 | H | H | OH |
| H | OH | H | H | H | OCH3 |
| CH3 | H | H | H | H | OH |
| H | OCH3 | H | H | OCH3 | OH |
| OCH3 | OH | H | H | H | H |
| H | H | OH | H | H | OH |
| H | H | H | H | OH | OH |
| CH3 | H | H | H | OH | OH |
| H | H | OH | OH | H | OH |
| OH | OH | H | H | OH | OH | and
(ii) a quinone dyestuff of the formula

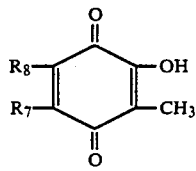

wherein $R_7$ and $R_8$ have the following indicated values

| R7 | R8 |
|---|---|
| OH | OCH3 |
| OCH3 | OCH3 |
| OH | H | said dyestuff being present in an amount ranging from 0.001 to 5 percent by weight based on the total weight of said composition, and (c) an anhydrous non-ionic surface-active agent present in an amount of at least 20 weight percent, said surface-active agent being selected from the group consisting of polyoxyethylenated fatty alcohol, polyoxyethylenated alkyl phenol, polyoxyethylenated naphthol and polyglycerolated fatty alcohol, said composition not containing more than 1 percent by weight of water.

3. A process for preserving a quinone dyestuff selected from the group of
(i) a quinone dyestuff of the formula

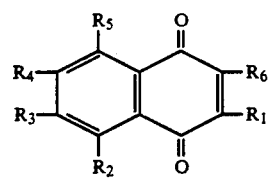

wherein $R_1$, $R_2$, $R_3$, $R_4$, $R_5$ and $R_6$ have the following indicated values

| R1 | R2 | R3 | R4 | R5 | R6 |
|---|---|---|---|---|---|
| H | H | H | H | H | OH |
| OH | H | H | H | H | OH |
| H | H | H | OH | H | OH |
| H | H | H | H | OCH3 | OH |
| OCH3 | H | H | H | H | OH |
| H | OH | H | H | H | OH |
| H | H | OCH3 | H | H | OH |
| H | OH | H | H | H | OCH3 |
| CH3 | H | H | H | H | OH |
| H | OCH3 | H | H | OCH3 | OH |
| OCH3 | OH | H | H | H | H |
| H | H | OH | H | H | OH |
| H | H | H | H | OH | OH |
| CH3 | H | H | H | OH | OH |
| H | H | OH | OH | H | OH |
| OH | OH | H | H | OH | OH | and
(ii) a quinone dyestuff of the formula

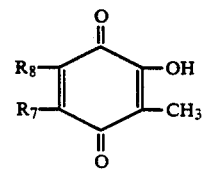

wherein $R_7$ and $R_8$ have the following indicated values:

| R7 | R8 |
|---|---|
| OH | OCH3 |
| OCH3 | OCH3 |
| OH | H | said process comprising dissolving said quinone dyestuff in an anhydrous solvent selected from the group consisting of a saturated alcohol, polyol, glycol ether, ester of an ethylene glycol monoalkyl ether and saturated fatty acid ester of a saturated lower alcohol together with a non-ionic surface-active agent, said quinone dyestuff being present in the resulting solution in an amount ranging from 0.001 to 5 percent by weight thereof, said anhydrous solvent being present in an amount of at least 15 weight percent thereof and said anhydrous non-ionic surface-active agent being present in an amount of at least 20 weight percent thereof.

4. The process of claim 3 wherein said anhydrous solvent is selected from the group consisting of ethanol, isopropanol, cetyl alcohol, ethylene glycol, propylene glycol, glycerol, diethylene glycol, ethylene glycol monoethyl ether, ethylene glycol monobutyl ether, diethylene glycol monoethyl ether, ethylene glycol monomethyl ether acetate, ethylene glycol monoethyl ether acetate, isopropyl myristate and isopropyl palmitate, and said non-ionic surface-active agent is selected from the group consisting of polyoxyethylenated fatty alcohol, polyoxyethyleneated alkyl phenol, polyoxyethyleneated naphthol and polyglycerolated fatty alcohol.

5. A process for dyeing hair comprising wetting said hair with water and contacting said wetted hair with an amount of the composition of claim 1 effective to dye said hair.

6. A process for preparing an aqueous hair-dyeing composition for immediate application to the hair so as to dye the same comprising dissolving in an aqueous medium a liquid or cream anhydrous composition consisting essential of
(a) an anhydrous solvent present in an amount of at least 15 weight percent, said solvent being selected from the group consisting of a saturated alcohol, polyol, glycol ether, ester of an ethylene glycol monoalkyl ether and saturated fatty acid ester of a saturated lower alcohol,
(b) a quinone dyestuff selected from the group consisting of
(i) a quinone dyestuff having the formula

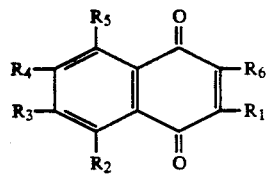

wherein $R_1$, $R_2$, $R_3$, $R_4$, $R_5$ and $R_6$ have the following indicated values:

| $R_1$ | $R_2$ | $R_3$ | $R_4$ | $R_5$ | $R_6$ |
|---|---|---|---|---|---|
| H | H | H | H | H | OH |
| OH | H | H | H | H | OH |
| H | H | H | OH | H | OH |
| H | H | H | H | $OCH_3$ | OH |
| $OCH_3$ | H | H | H | H | OH |
| H | OH | H | H | H | OH |
| H | H | $OCH_3$ | H | H | OH |
| H | OH | H | H | H | $OCH_3$ |
| $CH_3$ | H | H | H | H | OH |
| H | $OCH_3$ | H | H | $OCH_3$ | OH |
| $OCH_3$ | OH | H | H | H | H |
| H | H | OH | H | H | OH |
| H | H | H | H | OH | OH |
| $CH_3$ | H | H | H | OH | OH |
| H | H | OH | OH | H | OH |
| OH | OH | H | H | OH | OH | and
(ii) a quinone dyestuff of the formula

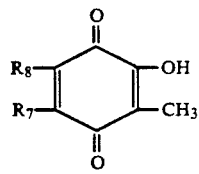

wherein $R_7$ and $R_8$ have the following indicated values

| $R_7$ | $R_8$ |
|---|---|
| OH | $OCH_3$ |
| $OCH_3$ | $OCH_3$ |
| OH | H | said dyestuff being present in an amount ranging from 0.001 to 5 percent by weight based on the total weight of said composition, and
(c) an anhydrous non-ionic surface-active agent present in an amount of at least 20 weight percent, the weight ratio of said composition to said aqueous medium ranging from 0.25:1 to 2:1, said composition not containing more than 1 percent by weight of water.

7. The process of claim 6 wherein said anhydrous solvent is selected from the group consisting of ethanol, isopropanol, cetyl alcohol, ethylene glycol, propylene glycol, glycerol, diethylene glycol, ethylene glycol monoethyl ether, ethylene glycol monobutyl ether, diethylene glycol monoethyl ether, ethylene glycol monomethyl ether acetate, ethylene glycol monoethyl ether acetate, isopropyl myristate and isopropyl palmitate, and said non-ionic surface active agent is selected from the group consisting of polyoxyethylenated fatty alcohol, polyoxyethylenated alkyl phenol, polyoxyethylenated naphthol and polyglycerolated fatty alcohol.

8. An anhydrous storage-stable liquid or cream composition consisting essentially of
(a) an anhydrous solvent present in an amount of at least 15 weight percent, said solvent being selected from the group consisting of a saturated alcohol, polyol, glycol ether, ester of an ethylene glycol monoalkyl ether and saturated fatty acid ester of a saturated lower alcohol,
(b) a quinone dyestuff selected rom the group consisting of
(i) a quinone dyestuff of the formula

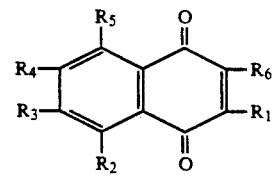

wherein $R_1$, $R_2$, $R_3$, $R_4$, $R_5$ and $R_6$ have the following indicated values:

| $R_1$ | $R_2$ | $R_3$ | $R_4$ | $R_5$ | $R_6$ |
|---|---|---|---|---|---|
| H | H | H | H | H | OH |
| OH | H | H | H | H | OH |
| H | H | H | OH | H | OH |
| H | H | H | H | $OCH_3$ | OH |
| $OCH_3$ | H | H | H | H | OH |
| H | OH | H | H | H | OH |
| H | H | $OCH_3$ | H | H | OH |
| H | OH | H | H | H | $OCH_3$ |
| $CH_3$ | H | H | H | H | OH |
| H | $OCH_3$ | H | H | $OCH_3$ | OH |
| $OCH_3$ | OH | H | H | H | H |
| H | H | OH | H | H | OH |
| H | H | H | H | OH | OH |
| $CH_3$ | H | H | H | OH | OH |
| H | H | OH | OH | H | OH |
| OH | OH | H | H | OH | OH | and
(ii) a quinone dyestuff of the formula

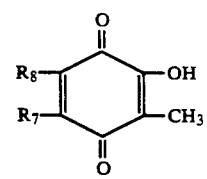

wherein $R_7$ and $R_8$ have the following indicated values

| $R_7$ | $R_8$ |
|---|---|
| OH | $OCH_3$ |

| R₇ | R₈ |
|---|---|
| OCH₃ | OCH₃ |
| OH | H | said dyestuff being present in an amount ranging from 0.001 to 5 percent by weight based on the total weight of said composition, and (c) an anhydrous non-ionic surface-active agent present in an amount of at least 20 weight percent, said surface-active agent being selected from the group consisting of nonylphenol oxyethylenated with 9 moles of ethylene oxide, nonylphenol oxyethylenated with 4 moles of ethylene oxide and cetyl-stearyl alcohol containing 15 moles of ethylene oxide, said composition not containing more than 1 percent by weight of water.

* * * * *